United States Patent [19]
Ondetti et al.

[11] 3,937,819
[45] Feb. 10, 1976

[54] METHOD OF STABILIZING AN INJECTABLE COMPOSITION OF A CHOLECYSTOKININ ACTIVE OCTAPEPTIDE

[75] Inventors: Miguel Angel Ondetti, Princeton; Charles Riffkin, Edison; Bernard Rubin, Lawrence Township; Aaron L. Weiss, East Brunswick, all of N.J.

[73] Assignee: E. R. Squibb & Sons, Inc., Princeton, N.J.

[22] Filed: July 22, 1974

[21] Appl. No.: 490,644

[52] U.S. Cl. .............................................. 424/177
[51] Int. Cl.² ................. A61K 37/00; C07C 103/52
[58] Field of Search ................... 424/177; 260/112.5

[56] References Cited
UNITED STATES PATENTS

| | | | |
|---|---|---|---|
| 3,723,406 | 3/1973 | Ondetti et al. | 260/112.5 |
| 3,734,946 | 5/1973 | Ondetti et al. | 260/112.5 |

OTHER PUBLICATIONS

Sollmann, "A Manual of Pharmacology," Saunders Co., Phila., 1957, pp. 6, 7, 549, 550.
Kosower, "Introduction to Physical Organic Chemistry," Wiley and Sons, New York, 1968, pp. 343–351.

*Primary Examiner*—Lewis Gotts
*Assistant Examiner*—Reginald J. Suyat
*Attorney, Agent, or Firm*—Lawrence S. Levinson; Merle J. Smith; Burton Rodney

[57] ABSTRACT

A stable composition of the sulfated octapeptide,

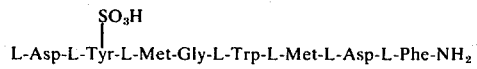

having cholecystokinin activity, is obtained by lyophilizing an aqueous solution of the octapeptide and NaCl.

1 Claim, No Drawings

METHOD OF STABILIZING AN INJECTABLE COMPOSITION OF A CHOLECYSTOKININ ACTIVE OCTAPEPTIDE

BACKGROUND OF THE INVENTION

The sulfated octapeptide

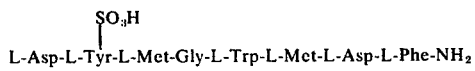

has been found to possess cholecystokinin activity. As such it stimulates gall bladder contraction and is useful as a diagnostic aid in x-ray examination of the gall bladder in the same manner as cholecystokinin. For such purposes the sulfated octapeptide may be dissolved in water for injection to form an injectable which is administered either intravenously or subcutaneously to mammalian species, e.g., dogs or cats.

OBJECTS OF THE INVENTION

It is an object of the present invention to provide compositions of

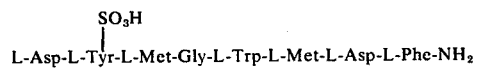

which are stable and retain the efficacy of the octapeptide during storage. Another object is to provide methods for preparing the stabilized compositions of the present invention. These and other objects of the present invention will be apparent from the following description.

SUMMARY OF THE INVENTION

A stable composition of the sulfated octapeptide

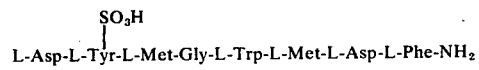

is obtained by lyophilizing an aqueous solution of the sulfated octapeptide and sodium chloride.

DETAILED DESCRIPTION

A stable composition of the sulfated octapeptide,

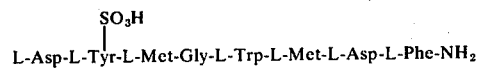

comprises a lyophilized powder of the sulfated octapeptide and sodium chloride.

The preparation of the sulfated octapeptide per se is described in U.S. Pats. 3,723,406 and 3,734,946. The disclosure of these patents are incorporated herein by reference. As indicated therein the sulfated octapeptide possesses cholecystokinin activity, that is it stimulates gall bladder contraction and so is useful as a diagnostic aid in X-ray examination of the gall bladder in the same manner as cholecystokinin.

The compositions of the present invention are prepared from an aqueous solution of the sulfated octapeptide and sodium chloride. A liter of this solution contains 2500 mcg and 21.43 g of sodium chloride. The pH is adjusted with sufficient sodium hydroxide (as 1 N solution) or hydrochloric acid (as 1 N solution), if necessary, to adjust the pH to from 5.50 to 6.50. The solution is brought to a volume of 1 liter by the addition of a sufficient quantity of water for injection.

The foregoing solution is sterilized by filtration, aseptically filled into sterile vials, lyophilized, and sealed after filling the head space in the vial with sterile filtered anhydrous nitrogen. The sealed vials are then stored at temperatures of 5°C or below.

The lyophilized composition contains the sulfated octapeptide and sodium chloride. It has been found convenient to fill the vials before lyophilization with 2.1 ml of a solution prepared as described above. The resulting vial after lyophilization then contains 5.25 mcg of sulfated octapeptide and 45.0 mg of sodium chloride.

The lyophilized material has excellent stability on storage and is readily reconstituted for injection by the addition of sterile water for injection. Preferably, the quantity of water for injection used for reconstitution is that amount which forms an isotonic solution.

The following example illustrates the present invention without, however, limiting the same thereto. The sulfated octapeptide in each of the following examples is

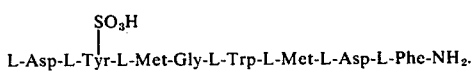

EXAMPLE

The solution is prepared by adding 2500 mcg of

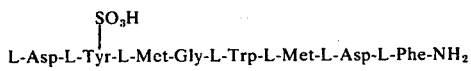

and 21.43 g of sodium chloride to about 900 ml of water for injection, USP. If necessary, the pH is adjusted to between 5.50 and 6.50 with addition of slight amount of either a 1 N solution of sodium hydroxide or a 1 N solution of hydrochloric acid. The volume is then adjusted to 1.0 liter by addition of water for injection, USP.

The solution is then filtered through a sterilizing membrane, and filled aseptically into 5 cc vials at 2.1 ml/vial. The vials are stoppered with fluted stoppers in the raised position and frozen. The vials are then lyophilized for 24 hours at a temperature of −30°C, then for 46 hours at a temperature of 25°C, and finally for one hour at a temperature of 37°C. The vials are then vented with dry sterile nitrogen and the stoppers placed in the closed position. The vials are then sealed and stored at a temperature of −20°C or lower.

The lyophilized vial is reconstituted by addition of 5 ml of sterile water for injection.

What is claimed is:

1. A method of enhancing the stability of the octapeptide

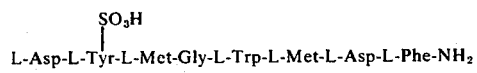

against degradation during storage, which comprises lyophilizing a solution containing per liter about 2500 mcg of said octapeptide and about 21.43 g of sodium chloride, and a sufficient quantity of water for injection to adjust the volume to about 1 liter, the pH of the solution being adjusted to from 5.50 to 6.50, if necessary, by addition of sodium hydroxide or hydrochloric acid.

* * * * *